United States Patent

Fouache et al.

[11] Patent Number: 6,048,976
[45] Date of Patent: Apr. 11, 2000

[54] PROCESS FOR THE PREPARATION OF CRYSTALLIZED MALTULOSE MONOHYDRATE

[75] Inventors: Catherine Fouache, Sailly Labourse; Jean-Christophe Choque, Bethune, both of France

[73] Assignee: Roquette Freres, Lestrem, France

[21] Appl. No.: 09/309,110

[22] Filed: May 10, 1999

[30] Foreign Application Priority Data

May 12, 1998 [FR] France .................................. 98 05951

[51] Int. Cl.[7] ....................................... C07H 1/06
[52] U.S. Cl. ...................... 536/127; 536/123.13; 536/124
[58] Field of Search .............................. 536/123.13, 124, 536/127

[56] References Cited

U.S. PATENT DOCUMENTS

Re. 30,820  12/1981  Walon ........................................ 435/94
3,691,013   9/1972   Sakai et al. .............................. 195/31

FOREIGN PATENT DOCUMENTS 48-077038 A2  10/1973  Japan .

OTHER PUBLICATIONS

Carbohydates. edited by Peter M. Collins, published by Chapman and Hall, pp. 293, 326 and 327, 1987.
P.E. Pferrer et al., Carbohydrate Research, 1983, 111, pp. 181–194.
L. Hough et al., Journal of the Chemical Society, 1953, pp. 2005–2009.
S. Peat et al., Biochemical Journal, 1952, vol. 51, pp. 17–18.
J.E. Hodge et al., Cereal Science Today, 1972, vol. 17, No. 7, pp. 180–188.

*Primary Examiner*—Howard C. Lee
*Attorney, Agent, or Firm*—Henderson & Sturm LLP

[57] ABSTRACT

The invention concerns a process for the preparation of crystallised maltulose monohydrate, characterised in that it comprises the steps of preparing an aqueous maltulose solution of a strength above 65% by weight, concentrating the aqueous maltulose solution to a dry matter ratio of more than 50% by weight and at a temperature such that the degree of maltulose supersaturation is less than 1, cooling the concentrated solution so as to take the degree of maltulose supersaturation to a value above 1, crystallising the maltulose in said supersaturated solution by cooling it at a controlled speed and by stirring, obtaining the separation, recuperation and drying of the maltulose monohydrate crystals.

10 Claims, No Drawings

PROCESS FOR THE PREPARATION OF CRYSTALLIZED MALTULOSE MONOHYDRATE

FIELD OF THE INVENTION

The present invention concerns a process for the preparation of maltulose monohydrate crystals by crystallisation of the maltulose in aqueous solution.

BACKGROUND OF THE INVENTION

Maltulose (4-O-α-D-glucopyranosyl-D-fructose) is not a product widely found in the natural world. It is found however in honey where it is synthesised by transglucosylation reaction during the hydrolysis of sucrose by D-glucosidases and also in yeasts, where it is produced by an equivalent enzymatic mechanism. Maltulose is also detected in waxy maize starch hydrolysates, and in the α-amylolysis hydrolysates of the glycogen in the liver of rats.

Maltulose has significant sweetening power, equivalent to that of maltitol, less than that of saccharose but greater than that of dextrose and maltose. Maltulose is used in the form of syrups in the food and pharmaceutical industries, and as a source material for various industrial syntheses.

The industrial preparation of a maltulose syrup is based on the isomerisation of a maltose syrup in an alkaline medium (HOUGH et al., 1953, *J. Chem. Soc.*, Part II, 2005; ROBERTS et al, *Biochem. J.*, 1952, 51, XVII). To illustrate such a process, the works of HODGE et al (*Cereal Science Today*, 1972, 17, 180) are worthy of mention, since they describe the preparation of a maltulose syrup by chemical isomerisation of a maltose syrup in the presence of sodium aluminate with conversion yields of about 95%.

Processes allowing maltulose syrups to be obtained by isomerisation of maltose enriched starch hydrolysates are also described in FR 2 055 645 and U.S. Pat. Reissue No. 30 280.

In terms of obtaining pure crystals of maltulose from these syrups, two processes are known, namely:
- the one described by HOUGH et al. in *J. Chem, Soc.*, 1953, Part II, 2005, with regard to the crystallisation of the maltulose monohydrate in the mixture dioxan-methanol, which produces a compound with a melting point (mp) of between 113 and 115° C.;
- the one described by PFEFFER and HICKS in *Carb. Research.*, 1983, 111, 181, describing the crystallisation of maltulose monohydrate in acetone. The crystals, washed in acetone and dried in the air, have an mp of 116.5 to 118° C.

It seems therefore clear from the prior art that maltulose crystallisation processes require the use of toxic and flammable organic solvents (dioxan-methanol, acetone) to obtain maltulose crystals. But the use of such solvents involves a degree of hazard for the people handling them, and indeed for the environment.

Above all, these processes demand a thorough purification of the crystallised maltulose so as to eliminate all traces of organic solvents. Indeed, these solvent traces would undoubtedly present toxicity within the scope of the food and pharmaceutical applications of the maltulose.

The previously described processes are not therefore satisfactory since they suffer the drawback of not being able to offer a straightforward method of producing maltulose crystals without traces of toxic compounds resulting from the crystallisation stage. Consequently, the crystallised maltulose obtained according to known processes cannot be directly used in pharmaceutical applications, for example for the manufacture of powders or tablets.

The object of the invention is thus to remedy this situation, and to propose a process which meets the various constraints of practice better than those which already exist.

Indeed, the applicants have managed to perfect an industrial process enabling crystallised maltulose to be obtained from an aqueous solution, and consequently free from all toxic compounds.

In doing this, the applicants have overcome a technical prejudice against the use of such a process using water as a solvent to crystallise the maltulose, since it has never been suggested that maltulose may be crystallised directly and easily in water and still less that the crystals thus formed can be isolated from it.

On the contrary, because of the high solubility of maltulose in water, specialists in this field concluded that the crystallisation of maltulose from an aqueous solution was difficult to achieve industrially. Thus, in the HAYASH-IBARA patent (FR 2 055 645) it is recalled that maltulose is very soluble in water and it is additionally stated that maltulose syrups are difficult to crystallise, even in very concentrated solutions, at the usual temperature. In the conditions described in this patent, the maltulose, when it crystallises, does so in the form of particles so fine and so poorly formed that they cannot in any case be separated out from the syrup.

This crystallisation in fact presents a certain number of technical difficulties, which the applicants have resolved after extensive research.

OBJECTS AND SUMMARY OF THE INVENTION

The object of the present invention is thus to propose a process for the preparation of maltulose crystals which is devoid of the above-mentioned drawbacks.

The process for the preparation of crystallised maltulose monohydrate is characterised in that it comprises the following stages:
- the preparation of an aqueous maltulose solution of a strength above 65% by weight,
- the concentration of the aqueous maltulose solution to a dry matter ratio of more than 50% by weight and at a temperature such that the degree of maltulose supersaturation is less than 1,
- the cooling of said concentrated solution so as to take the degree of maltulose supersaturation to a value above 1,
- the crystallisation of the maltulose in said supersaturated solution, by cooling it at a controlled speed and by stirring, and
- the separation, recuperation and drying of the maltulose monohydrate crystals thus obtained.

The process according to the invention therefore comprises a first stage of preparation of an aqueous maltulose solution of a strength above 65% by weight. The strongest solutions will quite obviously give the best crystallisation yields.

The enrichment of the maltulose solution may be achieved by all methods known per se, such as for example chromatographic methods. Preferably, this enrichment will be carried out so as to obtain a maltulose strength of more than 85% by weight, and more preferentially of between 85 and 97% by weight.

According to a preferential version of the invention, the aqueous maltulose solution is prepared by isomerisation in alkaline conditions of a maltose rich syrup.

For example, the isomerisation of a maltose rich syrup is achieved by the addition of boric acid in at least equimolar quantities. The pH is then set at a value above 10, preferably close to 11. Isomerisation is then carried out at a temperature of about 50° C., over a period of between 4 and 5 hours. At the end of this isomerisation reaction, the yield from the conversion of maltose to maltulose is above 80%.

The maltulose solution thus obtained is then cooled to a temperature of about 30° C., and its pH set at 2 by the addition of hydrochloric acid.

The residual boric acid is then eliminated. Several boric acid crystallisation jets are preferably carried out. For example, two crystallisation jets enable about 80% of the initial boric acid to be eliminated.

Molecular sieving is then, carried out on this maltulose solution. This molecular sieving stage may consist, for example, of a chromatographic separation stage or of a membrane separation stage.

The chromatographic stage is carried out in a way known per se, in a discontinuous or continuous way (simulated fluid bed), on adsorbents of the strong cationic resin type using alkaline or alkaline-earth ions, such as calcium or magnesium, but more preferentially using sodium ions and with the medium constituted by 4% divinyl benzylidene. The maltulose solution thus obtained is then demineralised.

The second stage in the process according to the invention consists in concentrating said aqueous maltulose solution to obtain a solution with a dry matter ratio above 50% by weight, at a temperature such that the degree of maltulose supersaturation is less than 1.

According to a preferential version of the invention, the maltulose solution obtained at the end of the second stage of the process has a dry matter ratio of between 65 and 75% by weight. This ratio will be able to be all the lower when the maltulose strength of the solution is higher.

This concentration stage is carried out in a way known per se, for example by evaporation of the water under vacuum at a temperature above 60° C., so as to obtain a concentrated solution with a degree of maltulose supersaturation less than 1.

An important characteristic of the process according to the invention is that at the end of this second stage, a concentrated aqueous maltulose solution is obtained at a temperature such that its degree of maltulose supersaturation has a value less than 1. This temperature will be preferentially between 60° C. and 80° C. for aqueous maltulose solutions of a strength greater than 65% by weight and of a dry matter ratio above 50% by weight.

The third stage of the process according to the invention then consists in cooling said solution so as to take the degree of maltulose supersaturation to a value above 1.

A degree of maltulose supersaturation slightly above 1, i.e. of between 1 and 1.2, more preferably of between 1.05 and 1.15 is reached by cooling the concentrated aqueous maltulose solution, obtained at the end of the second stage of the process according to the invention, to a value which will be a function of its initial maltulose content and of its dry matter ratio.

For example, the aqueous maltulose solutions of a strength above 65% by weight and of a dry matter ratio above 50% by weight are cooled to temperatures generally of between 20° C. and 50° C.

More particularly, the aqueous maltulose solutions of a strength between 85 and 97% by weight and a dry matter ratio between 65 and 75% by weight are cooled to temperatures of between 25° C. and 35° C.

The fourth stage of the process according to the invention, consists then in crystallising the maltulose in said supersaturated aqueous solution, by cooling it at a controlled speed and by stirring.

The other research conducted by the applicants to crystallise the maltulose in water has shown in fact that the other crystallisation processes consisting in varying the degree of maltulose supersaturation by techniques other than lowering the temperature, for example by evaporation of the water as practised in a process of evapocrystallisation, were not entirely satisfactory.

It is therefore to the credit of the applicants that they have shown that the solubility of maltulose decreases notably with the lowering of the temperature and that the degree of maltulose supersaturation is held at a value above 1 when the aqueous maltulose solution obtained at the end of the third stage is cooled slowly.

The fourth stage of the process according to the invention may be initiated by the formation of crystallisation seeds, which will be obtained by spontaneous nucleation or by seeding said aqueous maltulose solution.

According to a first preferential version of the invention, the choice is to lower the temperature of the aqueous maltulose solution obtained at the end of the third stage and to cause spontaneous nucleation by shearing the solution.

According to a second preferential version of the invention, the choice is to lower the temperature of the aqueous maltulose solution obtained at the end of the third stage and to seed it with maltulose crystals.

It is known by the person skilled in the art, generally speaking, that the speed of growth and the size of the crystals obtained may vary considerably with the speed at which the temperature is lowered.

Research conducted by the applicants has led it to establish a temperature drop profile, which causes the maltulose crystals to grow in an entirely satisfactory way.

Generally speaking, said maltulose solution is cooled from a temperature at the most equal to 50° C., preferentially from a temperature of between 25° C. and 35° C., to a temperature of at most 10° C., within at least 15 hours.

According to a preferential version of the process according to the invention, a maltulose solution of a strength above 90% by weight and of a dry matter ratio above 65% by weight is brought for example from 33° C. to 25° C. in less than 26 hours or else again, a maltulose solution of a strength above 70% by weight, and of a dry matter ratio above 50% by weight is brought from 25° C. to 15° C. in less than 24 hours.

This crystallisation stage of the maltulose may be carried out in a continuous or discontinuous way, for example in receptacles of the crystalliser type (horizontal mixers), cooled by double casing. Preferably said aqueous maltulose solution is poured into a receptacle of the crystalliser type, while being stirred, where the cooling is provided by circulation of water in the double wall.

Lastly, the maltulose monohydrate crystals are then collected by any method known per se by the person skilled in the art, for example, by centrifugation or filtration of the solution of crystallised maltulose.

Preferably, the crystals are then purified by washing in water or possibly with a little ethanol, then dried at a temperature lower than the melting point of the crystallised maltulose, preferentially at a temperature lower than 80° C., by any method known per se, for example in a drying chamber or on a fluidised bed.

The use of the process according to the invention allows crystals to be obtained of a size generally greater than 5 $\mu$m, preferentially of between 10 $\mu$m and 100 $\mu$m and of a strength above 90% and preferentially above 95%.

MORE DETAILED DESCRIPTION

Other characteristics and advantages of the invention will emerge from reading the non-restrictive examples described below.

EXAMPLE 1

Crystallisation of an aqueous maltulose solution of a strength of 95% by weight

An 87% maltulose solution is mixed with an equimolar quantity of boric acid, and the pH of the resulting solution is set at ii by addition of soda. The isomerisation of the maltose into maltulose is then carried out by heating said solution at 50° C. for 4 hours. The solution is finally cooled to 30° C. and its pH set at 2 by addition of hydrochloric acid.

At the end of this reaction, the yield from isomerisation of the maltose into maltulose is 86%.

Two crystallisation jets ensure the elimination of 80% of the initial boric acid. The maltulose solution is then purified by chromatography on strong cationic resin in the form of Na+, with the medium constituted by 4% divinyl benzylidene, followed by a demineralisation stage.

The 95% strength maltulose solution, obtained at the end of this first stage, is concentrated by evaporation under vacuum at a temperature of 60° C., to a dry matter ratio of about 67.5%. Its degree of supersaturation is then less than 1.

2 litres of this solution are cooled and brought to a temperature of 33° C., which leads to the obtention of a degree of maltulose supersaturation of a value of about 1.1.

Nucleation of the solution by shearing is then preferred, with a homogeneizer of the Ultra-Turrax type marketed by the BIOBLOCK company.

Cooling is then carried out linearly to 25° C. in 26 hours, in a double wall crystalliser, while being stirred.

At the end of crystallisation, the crystals are separated from the mother liquor using a conventional centrifugal dryer and weighed. During this stage, the 277g of crystals are washed with 300 ml of water then with 200 ml of ethanol.

The crystals are then dried in a fluidised bed dryer for 15 mins at 60° C.

The crystallisation yield is 15% by weight expressed by weight of crystallised maltulose over the original maltulose weight. The purity in maltulose of the crystals recuperated is 97% over dry. The moisture content is 5.4%.

EXAMPLE 2

Crystallisation of an aqueous maltulose solution of a strength of 75 % by weight Crystallisation is carried out from a 75% by weight maltulose solution obtained by the isomerisation of an aqueous maltose solution as described in example 1 and demineralised.

The solution is then concentrated to a dry matter ratio of 65% by evaporation under vacuum at a temperature of 60° C. and cooled to 25° C. to reach a degree of maltulose supersaturation above 1.

1 litre of this maltulose solution is seeded at 25° C. by the addition of 10 grammes of maltulose seeds as obtained in example 1.

The solution is then cooled to 15° C. in 24 hours. The crystallisation yield is 12% by weight. The purity of the maltulose monohydrate crystals recuperated is 95% over dry.

We claim:

1. An organic solvent free process for the preparation of crystallized maltulose monohydrate comprising the steps of:
   preparing an aqueous maltulose solution of a strength greater than about 65% of maltulose by weight;
   concentrating said aqueous maltulose solution to a dry matter ratio of greater than about 50% by weight of maltulose and at a temperature such that the degree of maltulose supersaturation is less than 1;
   cooling said concentrated aqueous maltulose solution to increase maltulose supersaturation to a value above 1;
   crystallizing the maltulose monohydrate in said supersaturated aqueous maltulose solution by cooling it at a controlled speed and by stirring; and p1 collecting the maltulose monohydrate crystals formed from said supersaturated aqueous maltulose solution and subsequently drying said crystals.

2. The process according to claim 1, wherein the aqueous maltulose solution is of a strength greater than abt 85% by weight.

3. The process according to claim 2, wherein the aqueous maltulose solution is of a strength between about 85% and about 97% by weight.

4. The process according to claim 1, wherein the aqueous maltulose solution is concentrated to a dry matter of between about 65% and about 75% by weight.

5. The process according to claim 1, wherein said concentrated aqueous maltulose solution is cooled to a temperature of between about 20° C. and about 50° C.

6. The process according to claim 1, wherein said concentrated aqueous maltulose solution is cooled to a temperature of between about 25° C. and about 50° C.

7. The process according to claim 1, wherein the maltulose is crystallized by causing spontaneous nucleation by shearing said supersaturated aqueous maltulose solution.

8. The process according to claim 1, wherein the maltulose is crystallized by seeding said supersaturated aqueous maltulose solution.

9. The process according to claim 1, wherein said supersaturated aqueous maltulose solution is cooled to a temperature not greater than 10° C. within at least 15 hours.

10. The process according to claim 1, wherein the maltulose monohydrate crystals are collected by centrifugation and dried at a temperature of between about 50° C. and about 80 ° C.

* * * * *